United States Patent
Yokota et al.

(10) Patent No.: US 8,913,812 B2
(45) Date of Patent: Dec. 16, 2014

(54) MEDICAL IMAGE PROCESSING APPARATUS

(71) Applicants: Tetsuya Yokota, Otawara (JP); Kensuke Shinoda, Otawara (JP); Satoshi Wakai, Nasushiobara (JP)

(72) Inventors: Tetsuya Yokota, Otawara (JP); Kensuke Shinoda, Otawara (JP); Satoshi Wakai, Nasushiobara (JP)

(73) Assignees: Kabushiki Kaisha Toshiba, Tokyo (JP); Toshiba Medical Systems Corporation, Otawara-shi (JP)

(*) Notice: Subject to any disclaimer, the term of this patent is extended or adjusted under 35 U.S.C. 154(b) by 223 days.

(21) Appl. No.: 13/693,233

(22) Filed: Dec. 4, 2012

(65) Prior Publication Data

US 2013/0094731 A1    Apr. 18, 2013

Related U.S. Application Data

(63) Continuation of application No. PCT/JP2011/078422, filed on Dec. 8, 2011.

(30) Foreign Application Priority Data

Dec. 15, 2010 (JP) .................... 2010-279675

(51) Int. Cl.
  *G06K 9/00* (2006.01)
  *G06K 9/46* (2006.01)
  *A61B 6/03* (2006.01)
  *A61B 6/00* (2006.01)

(52) U.S. Cl.
  CPC .............. *G06K 9/4671* (2013.01); *A61B 6/032* (2013.01); *A61B 6/463* (2013.01); *A61B 6/466* (2013.01); *A61B 6/481* (2013.01); *A61B 6/504* (2013.01); *A61B 6/507* (2013.01); *A61B 6/5217* (2013.01); *A61B 6/486* (2013.01)
  USPC ........................................................ 382/128

(58) Field of Classification Search
  None
  See application file for complete search history.

(56) References Cited

U.S. PATENT DOCUMENTS 5,148,809 A * 9/1992 Biegeleisen-Knight et al. ............................. 600/443
6,718,055 B1 * 4/2004 Suri ............................. 382/128

(Continued)

FOREIGN PATENT DOCUMENTS

JP    2005-095340    4/2005
JP    2006-081906    3/2006

(Continued)

OTHER PUBLICATIONS

Chinese Office Action issued May 6, 2014, in China Patent Application No. 201180004172.0.

(Continued)

*Primary Examiner* — Stephen R Koziol
*Assistant Examiner* — Jonathan S Lee
(74) *Attorney, Agent, or Firm* — Oblon, Spivak, McClelland, Maier & Neustadt, L.L.P.

(57) ABSTRACT

According to one embodiment, a medical image processing apparatus includes at least a vascular region extracting unit, a vascular shape image generating unit, a perfusion analyzing unit, a perfusion image generating unit, an image composition unit. The vascular region extracting unit extracts a vascular region based on a three-dimensional medical image. The vascular shape image generating unit generates an image of a vascular shape of the vascular region. The perfusion analyzing unit performs perfusion analysis on the three-dimensional medical image and obtains a perfusion value indicating a blood circulation condition in tissue around the vascular region. The perfusion image generating unit generates an image indicating the perfusion value. The image composition unit generates a vascular shape perfusion composition image in which an image of the vascular shape in a contraction portion in a blood vessel corresponding to the vascular region is combined with the image indicating the perfusion value.

15 Claims, 8 Drawing Sheets

(56) References Cited

U.S. PATENT DOCUMENTS

| | | |
|---|---|---|
| 7,583,829 B2 | 9/2009 | Kiraly et al. |
| 7,756,562 B2 | 7/2010 | Kimura |
| 7,774,041 B2 * | 8/2010 | Nambu et al. ............ 600/407 |
| 2006/0004279 A1 * | 1/2006 | Ikeda et al. ............... 600/411 |

FOREIGN PATENT DOCUMENTS

| | | |
|---|---|---|
| JP | 2009-195586 | 9/2009 |
| JP | 2010-125330 | 6/2010 |
| JP | 2010-178906 | 8/2010 |
| JP | 2011-212313 | 10/2011 |
| JP | 2011212313 A * | 10/2011 |
| WO | WO 2004/089218 A1 | 10/2004 |
| WO | WO 2006/002312 A2 | 1/2006 |
| WO | 2010/098444 | 9/2010 |

OTHER PUBLICATIONS

Japanese Office Action issued Jul. 22, 2014, in Japan Patent Application No. 2010-279675.

International Preliminary Report on Patentability and Written Opinion issued Jun. 18, 2013, in International application No. PCT/JP2011/078422 (English translation only).

International Search Report issued on Mar. 6, 2012 for PCT/JP2011/078422 filed on Dec. 8, 2011 with English Translation.

* cited by examiner

| PERFUSION VALUE | THRESHOLD OR LESS | | THRESHOLD OR MORE | |
|---|---|---|---|---|
| DIFFERENCE BETWEEN BOTH SIDES IN PERFUSION VALUES | LARGE | SMALL | LARGE | SMALL |
| RISK EVALUATION | HIGH | MIDDLE | MIDDLE | LOW |

FIG. 8

| | POSITION A | POSITION B | POSITION C |
|---|---|---|---|
| PERFUSION VALUE | THRESHOLD OR LESS | THRESHOLD OR LESS | THRESHOLD OR LESS |
| DIFFERENCE BETWEEN BOTH SIDES IN PERFUSION VALUES | SMALL | SMALL | LARGE |
| RISK EVALUATION | MIDDLE | MIDDLE | HIGH |

MEDICAL IMAGE PROCESSING APPARATUS

CROSS-REFERENCE TO RELATED APPLICATIONS

This application is a Continuation Application of No. PCT/JP2011/078422, filed on Dec. 8, 2011, and the PCT application is based upon and claims the benefit of priority from Japanese Patent Application No. 2010-279675, filed on Dec. 15, 2010, the entire contents of which are incorporated herein by reference.

FIELD

Embodiments described herein relate generally to a medical image processing apparatus.

BACKGROUND

Cerebral vascular contraction, a symptom that a blood vessel of a brain narrows, appears four to 14 days after the onset of subarachnoid hemorrhage. It is believed that almost all the cases of subarachnoid hemorrhage are accompanied by the symptom. When cerebral vascular contraction develops and a blood vessel of a brain narrows, often a cerebral infraction is caused. Thus, it is required to early and reliably identify a contraction portion of a cerebral blood vessel.

As a method for determining whether cerebral vascular contraction is present, a transcranial Doppler examination is conducted. In this examination, if an average blood flow rate of a horizontal segment of a middle cerebral artery is higher than usual, development of vascular contraction is suspected. Then, an examination that uses a constant medium or MR (magnetic resonance) is carried out to determine whether the vascular contraction has developed. Examples of determining examinations include three-dimensional CT angiography (CTA) and CT perfusion (CTP) that use constant media, MRA (Magnetic Resonance Angiography) and MRI (Magnetic Resonance Imaging) that use magnetic resonance, and SPECT (Single Photon Emission Computed Tomography). One or more images photographed in these examinations are used for determination. In particular, since combined use of CTA and CTP is low-invasive to patients as well as this examination is performed quickly and easily, attention is being paid to the usefulness.

CTP can determine a perfusion value of blood flowing from a blood vessel into capillary vessels in tissue. As perfusion values, values indicating blood circulation of capillary vessels in tissue can be used. Such values include a cerebral blood flow (CBF) per unit volume in cerebral tissue and per unit time, a cerebral blood volume (CBV) being a blood amount per unit volume in cerebral tissue, a mean transit time (MTT) of a blood flow in cerebral tissue, and the like. Each of CBF, CBV and MTT can be calculated based on variations over time in concentration of an injected constant medium in cerebral artery and cerebral tissue parts.

In CTA, an observer moves an image to search for a contraction portion without information of a position of a contraction in cerebral blood vessels. Therefore, the observer may overlook a contraction portion in dense cerebral blood vessels. Also, depending on a display condition of CTA, a contraction portion of a cerebral blood vessel may not be seen on a CTA image. Also, conventionally, even if CTA and CTP are combined with each other, a vascular shape and a blood circulation condition are not displayed on a screen at the same time, so that it is challenging to determine a position of a vascular contraction that causes a deteriorated condition of blood circulation. Also, if both examination images of CTA and CTP are simply arranged and displayed, when a risk of the onset of cerebral infraction at the vascular contraction portion is evaluated, the evaluation may depend on the observer's subjective, and thereby quantitative evaluation cannot be done.

BRIEF DESCRIPTION OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 8 is a view illustrating an indicator for evaluating a risk by the risk evaluating unit;

FIG. 9 is an exemplary list of risk evaluations obtained by the risk evaluating unit;

DETAILED DESCRIPTION

Hereinbelow, a description will be given of a medical image processing apparatus according to embodiments of the present invention with reference to the drawings.

In general, according to one embodiment, a medical image processing apparatus includes an image acquiring unit, a vascular region extracting unit, a vascular shape image generating unit, a perfusion analyzing unit, a perfusion image generating unit, an image composition unit, and a display unit. The image acquiring unit acquires a three-dimensional medical image. The vascular region extracting unit extracts a vascular region based on the three-dimensional medical image acquired by the image acquiring unit. The vascular shape image generating unit generates an image of a vascular shape of the vascular region extracted by the vascular region extracting unit. The perfusion analyzing unit performs perfusion analysis on the three-dimensional medical image acquired by the image acquiring unit. Then the perfusion analyzing unit obtains a perfusion value indicating a blood circulation condition in tissue around the vascular region. The perfusion image generating unit generates an image indicating the perfusion value obtained by the perfusion analyzing unit. The image composition unit generates a vascular shape perfusion composition image in which an image generated by the vascular shape image generating unit of the vascular shape in a contraction portion in a blood vessel corresponding to the vascular region is combined with the image indicating the perfusion value generated by the perfusion image generating unit. The display unit displays the vascular shape perfusion composition image combined by the image composition unit.

Figure 1:
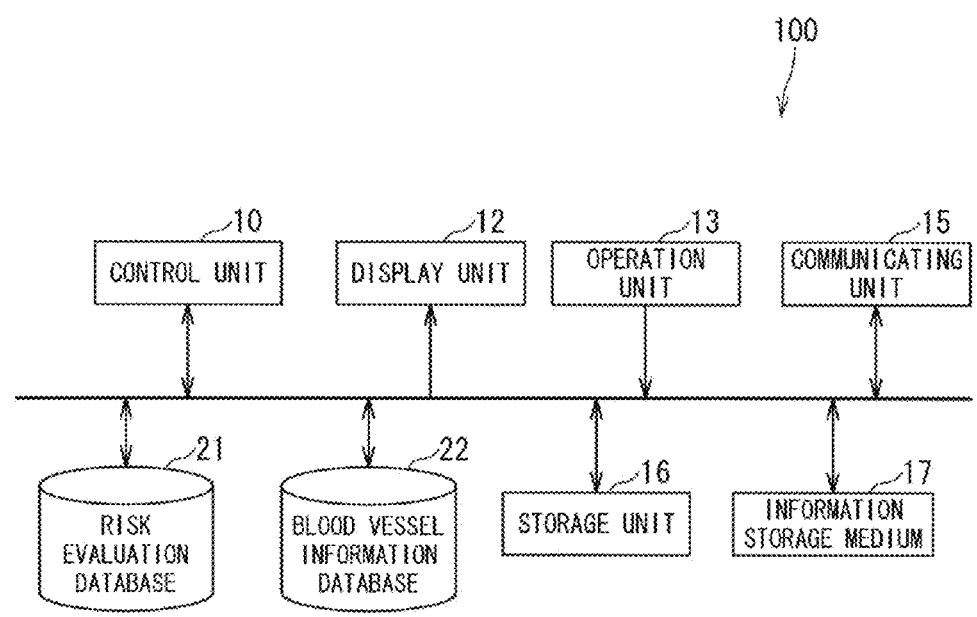
FIG. 1 is a schematic block diagram illustrating a medical image processing apparatus according to an embodiment of the present invention.

FIG. 1 is a schematic block diagram illustrating a medical image processing apparatus 100 according to an embodiment of the present invention. The medical image processing apparatus 100 is based on a personal computer or a workstation. Also, the medical image processing apparatus 100 may be a function in a modality. The medical image processing apparatus 100 includes a control unit 10, a display unit 12, an operation unit 13, a communicating unit 15, a storage unit 16, an information storage medium 17, a risk evaluation database 21, and a blood vessel information database 22. These components are connected to each other via a bus so that they can communicate with each other. In the present embodiment, a description will be made using medical images of a brain.

The display unit 12 is a monitor or the like. The operation unit 13 is an inputting device such as operation keys and a mouse. The communicating unit 15 is connected to a LAN in a hospital to communicate with other modalities.

The storage unit 16 functions as a work region for the control unit 10, the communicating unit 15, and the like. The storage unit 16 may be a RAM (Random Access Memory).

In the information storage medium 17 (computer-readable medium), a program and data are stored. The information storage medium 17 may be a hard disk drive or a memory (Flash Memory, ROM: Read Only Memory). In the information storage medium 17, a program for allowing a computer to function as each unit in the embodiment (a program for allowing a computer to perform processing of each unit), and a plurality of applications are stored.

The control unit 10 controls the entire apparatus. For example, the control unit 10 is a calculating unit that performs processing in accordance with a basic program such as an OS (Operating System) and a predetermined program. The control unit 10 carries out a variety of processes in the embodiment on the basis of programs (data) stored in the information storage medium 17.

In the risk evaluation database 21, a threshold value used for determining whether a risk of a perfusion value obtained by a perfusion analyzing unit 33 described later is high or not is stored. Also, a threshold value used for determining whether a risk of a difference between perfusion values of both the sides of a brain is high or not is stored. The stored threshold values are used to evaluate a risk.

In the blood vessel information database 22, a 3D angiogram including a vascular region, a two-dimensional image of a vascular shape, and data of perfusion values of blood vessels are stored.

Figure 2:
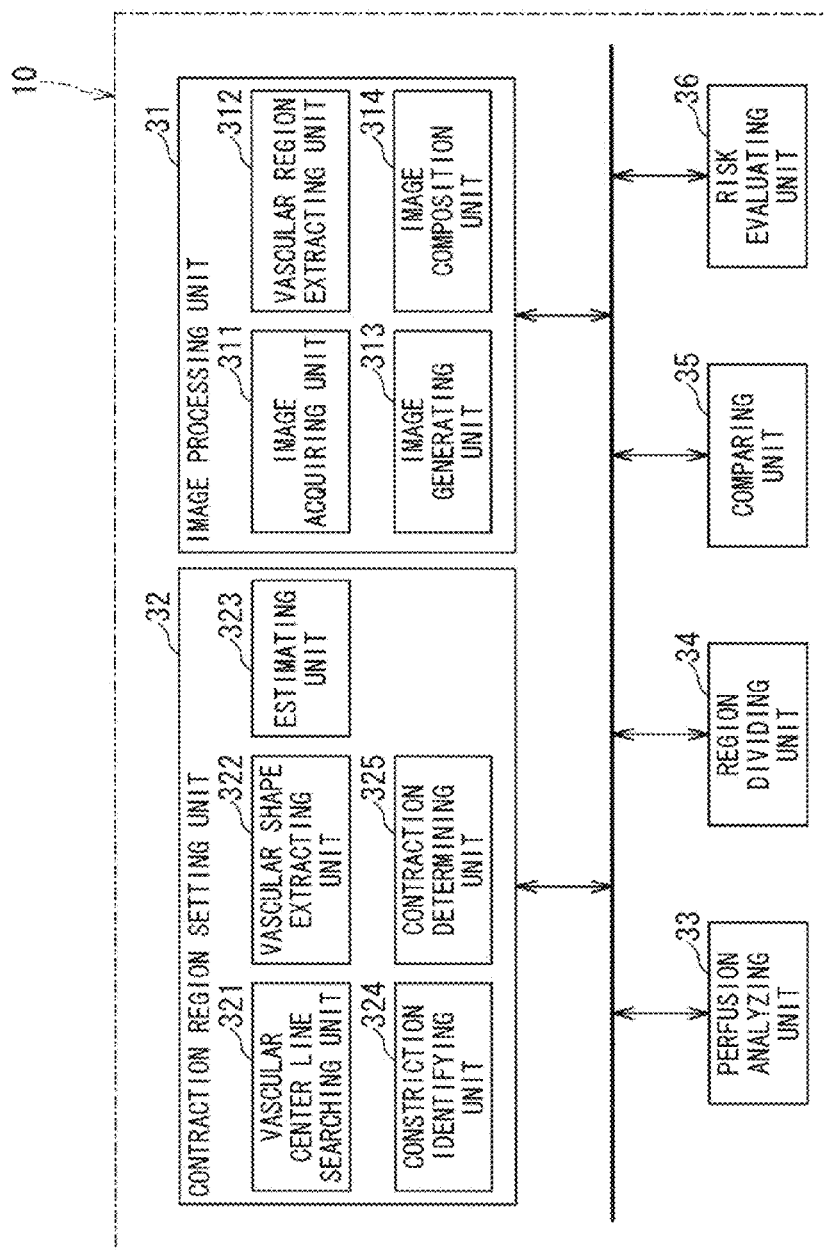
FIG. 2 is a view illustrating a detailed block diagram of the control unit.

FIG. 2 illustrates a detailed block diagram of the control unit 10. The control unit 10 includes an image processing unit 31, a contraction region setting unit 32, the perfusion analyzing unit 33, a region dividing unit 34, a comparing unit 35, and a risk evaluating unit 36.

The image processing unit 31 includes an image acquiring unit 311, a vascular region extracting unit 312, an image generating unit 313, and an image composition unit 314. The image acquiring unit 311 acquires 3D angiogram data of a brain or the like photographed by, for example, an exterior 3D-CT apparatus, via the communicating unit 15. The vascular region extracting unit 312 extracts a vascular region corresponding to a blood vessel from angiogram data. The image generating unit 313 generates a two-dimensional blood vessel image of a vascular region including a contraction portion extracted by the contraction region setting unit 32, from a vascular region, a 3D image, extracted by the vascular region extracting unit 312. The two-dimensional blood vessel image has a shape of a curved-surface cross-section of a blood vessel along a blood flow direction. A detail thereof will be described later. The image composition unit 314 combines a two-dimensional blood vessel image generated by the image generating unit 313 with an image indicating perfusion values obtained by the perfusion analyzing unit 33 described later.

The contraction region setting unit 32 includes a vascular center line searching unit 321, a vascular shape extracting unit 322, an estimating unit 323, a constriction identifying unit 324, and a contraction determining unit 325. The vascular center line searching unit 321 extracts a vascular center line from a vascular region extracted by the vascular region extracting unit 312. The vascular shape extracting unit 322 extracts an interior wall and an exterior wall of a present blood vessel on the basis of a vascular center line extracted by the vascular center line searching unit 321.

The estimating unit 323 estimates a vascular interior wall of a normal blood vessel by variations in cross-sectional area of a vascular interior wall along a vascular center line extracted by the vascular center line searching unit 321. The constriction identifying unit 324 identifies a constricted portion of blood vessel on the basis of a difference between an interior wall of a present blood vessel extracted by the vascular shape extracting unit 322 and an interior wall of a normal blood vessel estimated by the estimating unit 323.

The contraction determining unit 325 determines whether a constricted portion identified by the constriction identifying unit 324 is vascular contraction by analyzing properties between vascular interior and exterior walls.

The perfusion analyzing unit 33 analyzes a condition of a blood flow by perfusion analysis based on data of a plurality of time-series 3D angiograms acquired by the image acquiring unit 311. Specifically, the perfusion analyzing unit 33 determines perfusion values (information indicating conditions of blood circulation such as CBF, CBV, and MTT) based on information about change of a pixel value corresponding to a cerebral artery part of angiogram data (a value corresponding to a concentration of a constant medium) and change of a pixel value corresponding to a cerebral tissue part over time.

The region dividing unit 34 divides a medical image of a brain acquired by the image acquiring unit 311 into both sides along a cerebral midline.

The comparing unit 35 compares perfusion values of both the sides divided by the region dividing unit 34 with each other. Also, the comparing unit 35 compares perfusion values obtained in an examination of the past and stored in the blood vessel information database 22, with a perfusion value obtained in a present examination.

The risk evaluating unit 36 evaluates a risk on the basis of perfusion values obtained by the perfusion analyzing unit 33 and a value of a difference between both the sides in perfusion values obtained by the comparing unit 35.

Next, an operation of the foregoing medical image processing apparatus will be described. In the embodiment, angiogram data of a cerebral blood vessel will be handled. First, an operation to extract a contraction portion of a blood vessel will be described with reference to FIG. 3.

An exterior 3D-CT apparatus has photographed angiogram data of a head of an object to which a constant medium was injected. The image acquiring unit 311 of the control unit 10 acquires the 3D angiogram data of the head via the communicating unit 15 (step S101). Then, the vascular region extracting unit 312 extracts a vascular region from the angiogram data of the head acquired by the image acquiring unit 311 in step S101 (step S103). Next, the vascular center line searching unit 321 of the contraction region setting unit 32 extracts a center line of a blood vessel from the vascular region extracted in step S103 (step S105). Then, the vascular shape extracting unit 322 extracts present vascular interior and exterior walls by a region growing method (step S107). The extraction is based on the center line of the blood vessel extracted by the vascular center line searching unit 321 in step S105.

Next, the estimating unit 323 estimates a vascular interior wall of a normal blood vessel (step S109). The estimation is based on variations in cross-sectional area of the vascular interior wall along the vascular center line extracted by the vascular center line searching unit 321 in step S105. Next, the constriction identifying unit 324 takes a difference in cross-sectional areas between the interior wall of the present blood vessel extracted in step S107 and the normal vascular interior wall estimated in step S109. The constriction identifying unit 324 then identifies a portion with the difference greater than a predetermined value as a vascular constricted region (step S111).

Next, the contraction determining unit 325 analyzes properties of the interior wall of the blood vessel in the constricted region identified by the constriction identifying unit 324 and properties of the exterior wall of the present blood vessel, in the same portion, extracted by the vascular shape extracting unit 322 to determine whether the constricted region is caused by a plaque (fat or fiber accumulated in a blood vessel) or by vascular contraction (step S113). It should be noted that an operator may visually observe an image to determine a vascular contraction portion.

Next, an operation to analyze perfusion values to extract a low perfusion region will be described with reference to FIG. 4.

The perfusion analyzing unit 33 performs perfusion analysis based on the data of the time-series angiograms of the head acquired by the image acquiring unit 311 in step S101 and calculates CBF, CBV, and MTT (step S201) to determine perfusion values of the whole brain (step S203). Next, the perfusion analyzing unit 33 extracts, from the perfusion values of the whole brain calculated in step S203, a region of blood circulation with a perfusion value equal to or lower than the threshold value stored in the risk evaluation database 21 (low perfusion region) (step S205).

Figure 5:
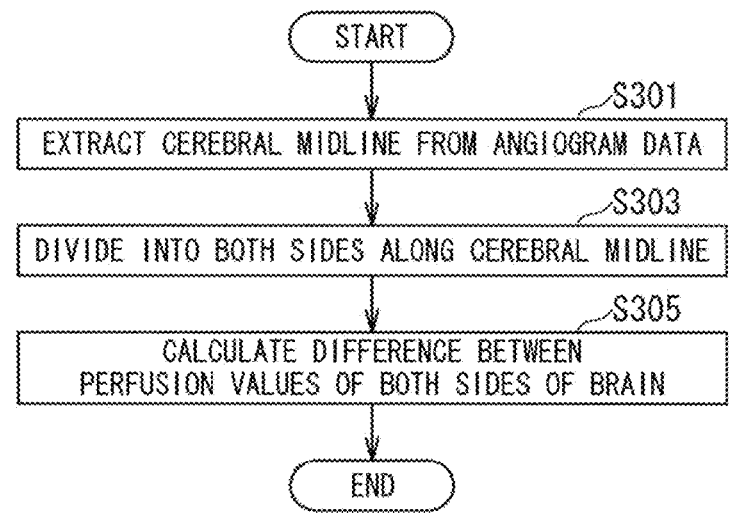
FIG. 5 is a flow chart showing a procedure for determining a perfusion value difference between both the sides of brain.

Next, an operation to determine a perfusion value difference between both the sides of brain will be described with reference to FIG. 5.

The region dividing unit 34 extracts a cerebral midline from 3D angiogram data of the head at any time phase, the data being acquired by the image acquiring unit 311 (step S301). The region dividing unit 34 extracts the whole cerebral region, thereafter dividing the extracted region into both sides along the cerebral midline (step S303). Next, the comparing unit 35 compares perfusion values of both the sides with each other to calculate a difference therebetween (step S305). The perfusion values of both the sides are included in the perfusion values of the whole brain calculated by the perfusion analyzing unit 33 in step S203 and the sides are divided by the region dividing unit 34 in step S303.

Figure 6:
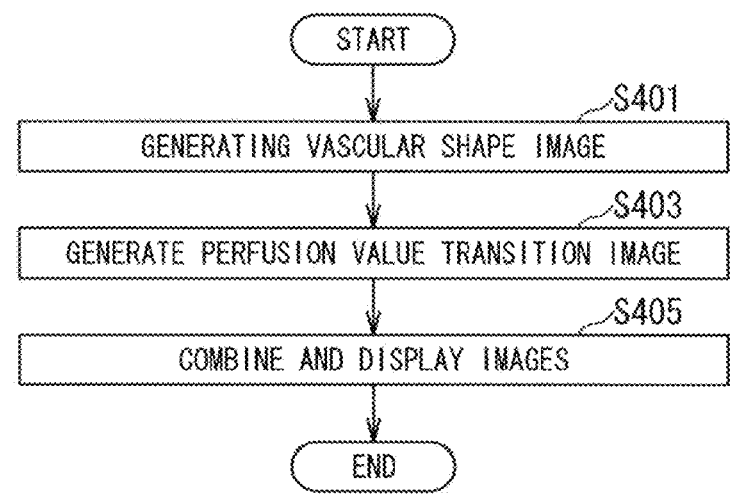
FIG. 6 is a flow chart showing a procedure for displaying a combination of vascular contraction and perfusion values.

Next, an operation to display a combination of vascular contraction and perfusion values will be described with reference to FIG. 6.

Figure 3:
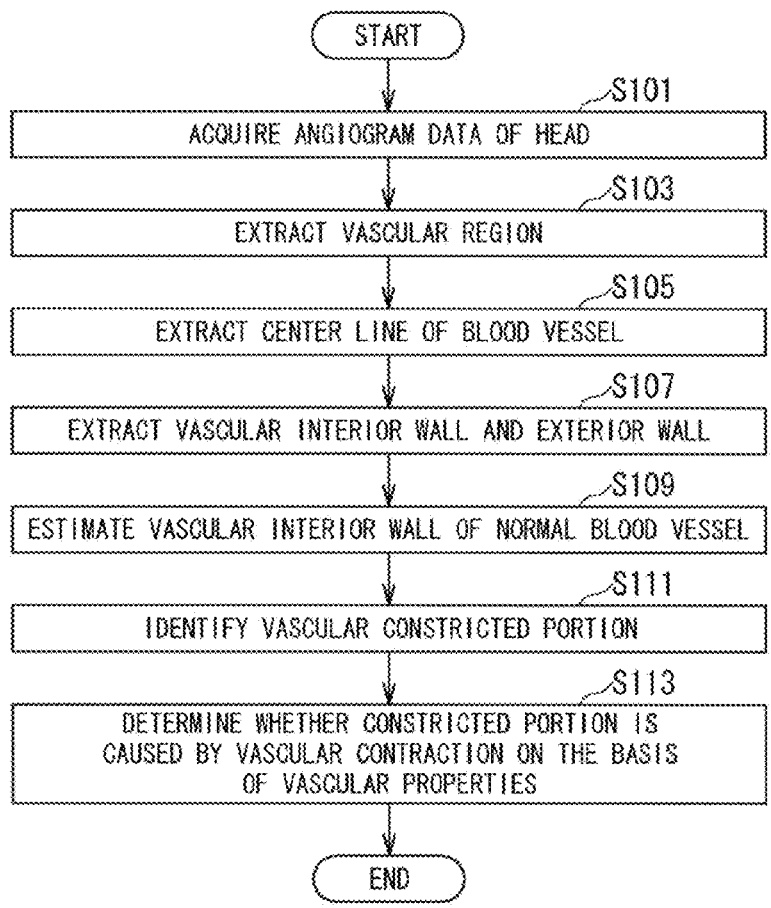
FIG. 3 is a flow chart showing a procedure for extracting a contraction portion of a blood vessel.

The image generating unit 313 generates a two-dimensional vascular shape image of a particular position (referred to as the position A) determined to be vascular contraction in step S113 of FIG. 3 and an area around the position A (step S401). In the embodiment, a Stretch MPR (Multi Planar Reconstruction) image of a cross-section of a blood vessel along the blood flow direction, the shape of a stretched blood vessel, is generated. At this time, in the Stretch MPR image, the interior wall extracted in step S107, of the present blood vessel with contraction and the interior wall estimated in step S109, of the normal blood vessel are displayed at the same time.

Figure 4:
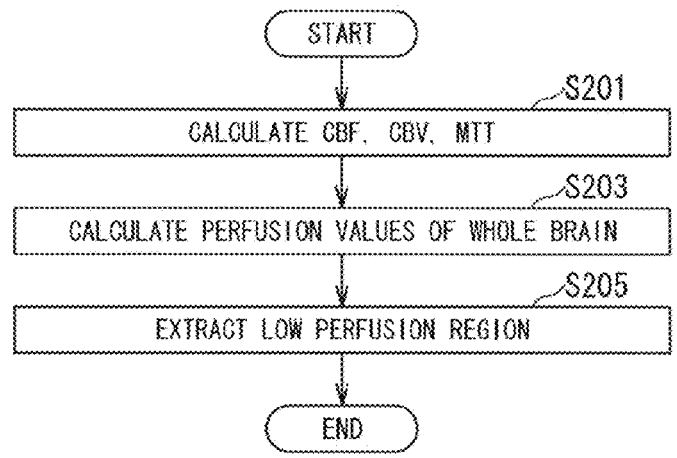
FIG. 4 is a flow chart showing a procedure for analyzing perfusion values to extract a low perfusion region.

Also, the image generating unit 313 generates a two-dimensional perfusion value image indicating perfusion values of the position A and the area around the position A, from the perfusion values obtained in FIG. 4 (step S403). Then, the image composition unit 314 combines the Stretch MPR image at the position A generated in step S401 with the perfusion value image generated in step S403, and displays the resultant image on the display unit 12 (step S405). At this time, for example, among the perfusion values of the whole brain calculated in step S203, only a region of blood circulation with a perfusion value equal to or lower than the threshold value stored in the risk evaluation database 21 (low perfusion region) may be displayed.

Figure 7:
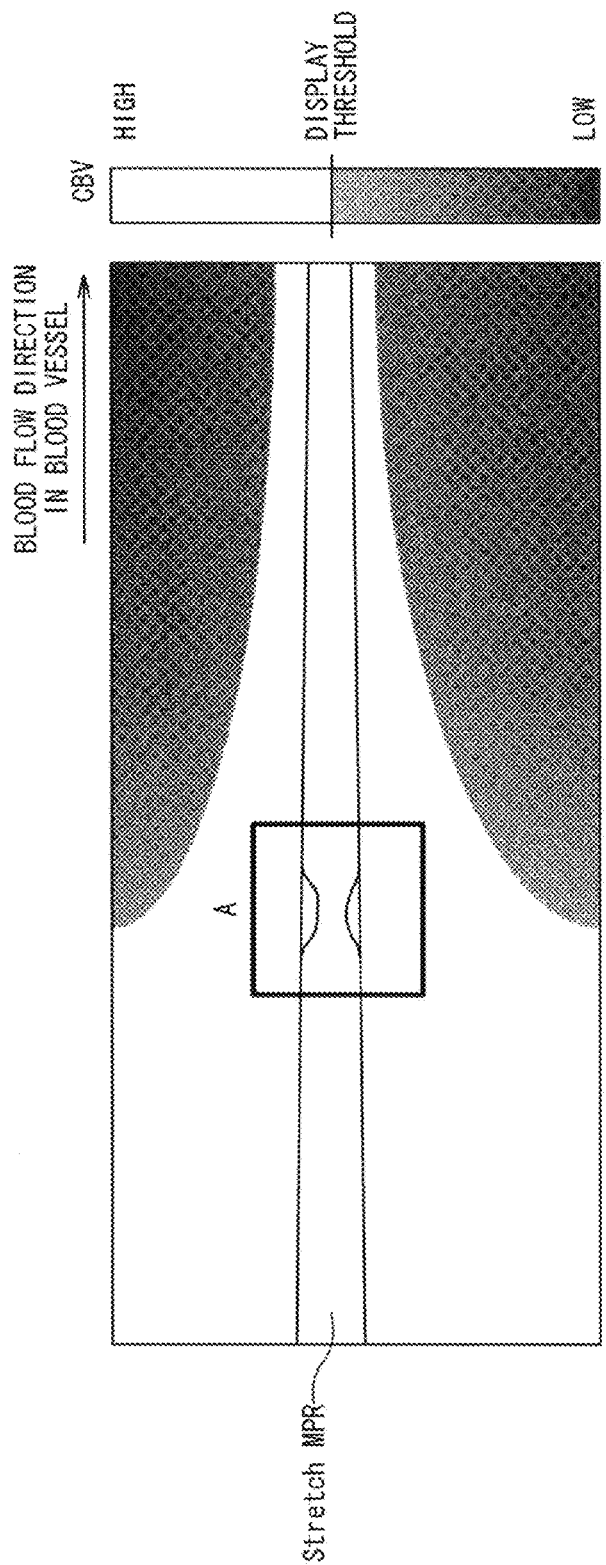
FIG. 7 is a view illustrating an example of a composition image of a vascular shape image (Stretch MPR image) at the vascular contraction position A and a perfusion value image indicating perfusion values equal to or less than a predetermined threshold value.

FIG. 7 illustrates an example of a composition image of a vascular shape image (Stretch MPR image) at the vascular contraction position A and a perfusion value image indicating perfusion values equal to or less than a predetermined threshold value. At the vascular contraction position A, variations in cross-sectional area of the vascular interior wall are irregular, and the present vascular shape in which the interior wall is raised and the estimated vascular shape in which variations in cross-sectional area of the interior wall are constant and the interior wall is not raised are displayed. Also, blood perfusion in cerebral tissue is indicated around the stretched vascular shape. The perfusion values in FIG. 7 equal to or less than the predetermined threshold value are colored in a colored bar, and as a perfusion value is lower, the color becomes dark. In FIG. 7, if it is assumed that a blood flow direction is from left to right, as blood goes to right from the vascular contraction position A, regions of low perfusion values become closer to the blood vessel. It is because the contraction of the position A causes the blood flowing after the contraction portion to be sluggish, and thus blood perfusion into the cerebral tissue becomes gradually sluggish.

It should be noted that a vascular shape image is not limited to a Stretch MPR image, and may be a Curved MPR image, being a curved cross-section, or other shape images.

Also, at a vascular contraction position in the brain, there is need for evaluating whether the contraction has a high risk of lesion such as cerebral infraction and considering the necessity of treatment. FIG. 8 illustrates an indicator for evaluating a risk by the risk evaluating unit 36. At a vascular contraction position and around the position, if a perfusion value is equal to or less than a predetermined threshold value and a difference between both sides in perfusion values is greater than a predetermined threshold values, the risk evaluating unit 36 assigns "high" to the risk and evaluates the position to be preferentially treated. If a perfusion value is equal to or less than the predetermined threshold value and a difference between both sides in perfusion values is smaller than the predetermined threshold value, or if a perfusion value is equal to or greater than the predetermined threshold value and a difference between both sides in perfusion values is greater than the predetermined threshold value, the risk evaluating unit 36 assigns "middle" to the risk and evaluates the contraction to be watched. If a perfusion value is greater than the predetermined threshold value and a difference between both sides in perfusion values is smaller than the predetermined threshold value, the risk evaluating unit 36 assigns "low" to the risk and evaluates the contraction to be minor.

FIG. 9 is an exemplary list of risk evaluations obtained by the risk evaluating unit 36. The risk evaluating unit 36 evaluates a risk on the basis of whether or not a perfusion value and a difference between both sides in perfusion values of each of vascular contraction positions A, B, and C are each equal to or less than the threshold values stored in the risk evaluation database 21.

In FIG. 9, lowering of perfusion values at the position A and the position B is equal to or less than the predetermined threshold value, but since differences between the perfusion values of both the sides are smaller than the predetermined threshold value, the risk evaluating unit 36 assigns "middle" to the risk. At the position C, since lowering of a perfusion value is equal to or less than the predetermined threshold values and a difference between the perfusion values of both the sides is greater than the predetermined threshold value, the risk evaluating unit 36 assigns "high" to the risk. Thus, the position C can be judged to be a vascular contraction having the highest risk.

Figure 10:
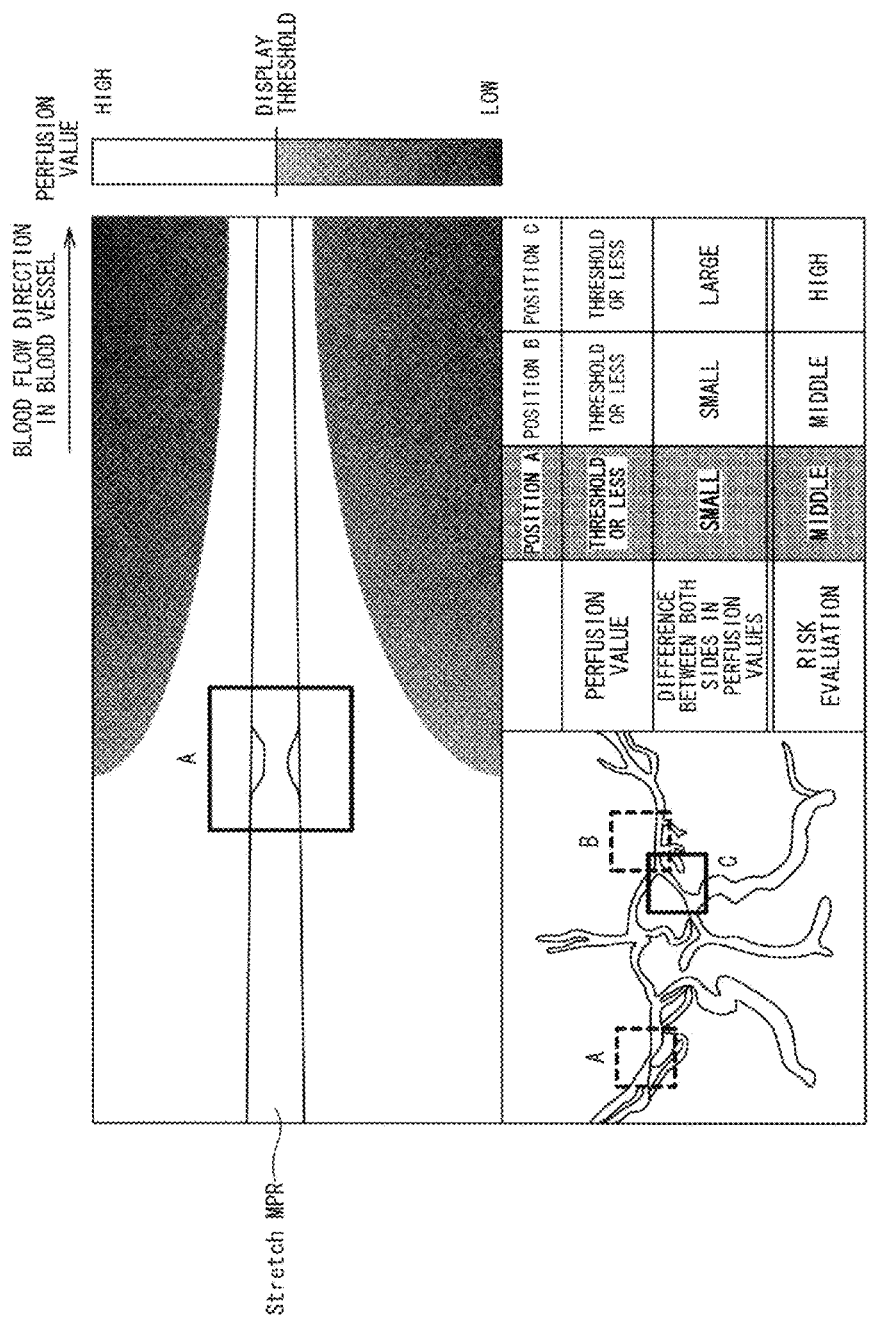
FIG. 10 is a view illustrating an example in which a composition image of a vascular shape image and a perfusion value image, a list of risk evaluations, and 3D angiogram data are displayed at a time.

At least the list of risk evaluations shown in FIG. 9 or 3D angiogram data corresponding to a position of vascular contraction may be displayed in connection with the composition image of the vascular shape image and the perfusion value image, shown in FIG. 7. FIG. 10 illustrates an example in which a composition image of a vascular shape image and a perfusion value image, a list of risk evaluations, and 3D angiogram data are displayed at a time. In FIG. 10, a composition image at the position A is displayed and in the list of risk evaluations, a corresponding column of the position A is highlighted. On a screen, a composition image, the list of risk evaluations, 3D angiogram data may be coordinated. For example, when a predetermined position on 3D angiogram data is designated, a corresponding composition image of a vascular shape image and a perfusion value image may be displayed, and a corresponding column at a predetermined position in the list of risk evaluations may be highlighted. Also, positions of the contraction positions A, B, and C in the 3D angiogram are boxed, and the position C with the risk evaluation being "high" may be made prominent on the 3D angiogram data as compared with the others.

Also, the image composition unit 314 may combine a composition image of a vascular shape image and a perfusion value image with a vascular wall image (three-dimensional vascular wall image) of a 3D angiogram. A three-dimensional vascular wall image may include, of a 3D angiogram, a vicinity of an exterior wall of the vascular wall (a region outside the vascular wall and within a predetermined distance from the exterior wall of the vascular wall). If 3D images of a vascular wall and a vicinity of an exterior wall are combined, a user can easily understand a boundary between a blood vessel and other tissue.

At this time, a perfusion value image may be further disposed in a place other than the vascular shape image and the 3D image of the vascular wall (and the 3D image of the vicinity of the vascular exterior wall). In this case, because the perfusion value image does not overlap the vascular shape image and the 3D image of the vascular wall (and the 3D image of the vicinity of the vascular exterior wall), the user can more easily understand a boundary between the blood vessel and other tissue. Also, if the perfusion value image does not overlap the vascular shape image and the 3D image of the vascular wall (and the 3D image of the vicinity of the vascular exterior wall), the user can accurately understand properties of the vascular wall.

In addition, a degree of recovery from an examination of the past to a present examination may be displayed on the display unit 12. In this case, first, 3D angiogram data obtained in an examination of the past and stored in the blood vessel information database 22 is aligned with 3D angiogram data of a present examination. For example, a cranium region is extracted from a head region by thresholding, and the cranium regions extracted from the two 3D angiogram data items are linearly aligned with each other. Further, cerebral regions may be non-linearly aligned with each other by using anatomical information to improve alignment accuracy.

After the alignment, the comparing unit 35 calculates a difference between perfusion values around a contraction position of a blood vessel, obtained in the examination of the past and stored in the blood vessel information database 22, and the perfusion values obtained in the present examination to determine whether the perfusion values of the portion in the blood vessel has been improved. Then, the risk evaluating unit 36 evaluates a risk on the basis of the perfusion value obtained by the perfusion analyzing unit 33 and the difference between the perfusion values of the present examination and the examination of the past, compared by the comparing unit 35. For example, as compared with the perfusion values in the examination of the past, if the perfusion value in the present examination has been improved by at least a predetermined threshold, the risk evaluating unit 36 lowers the risk of a lesion.

Figure 11:
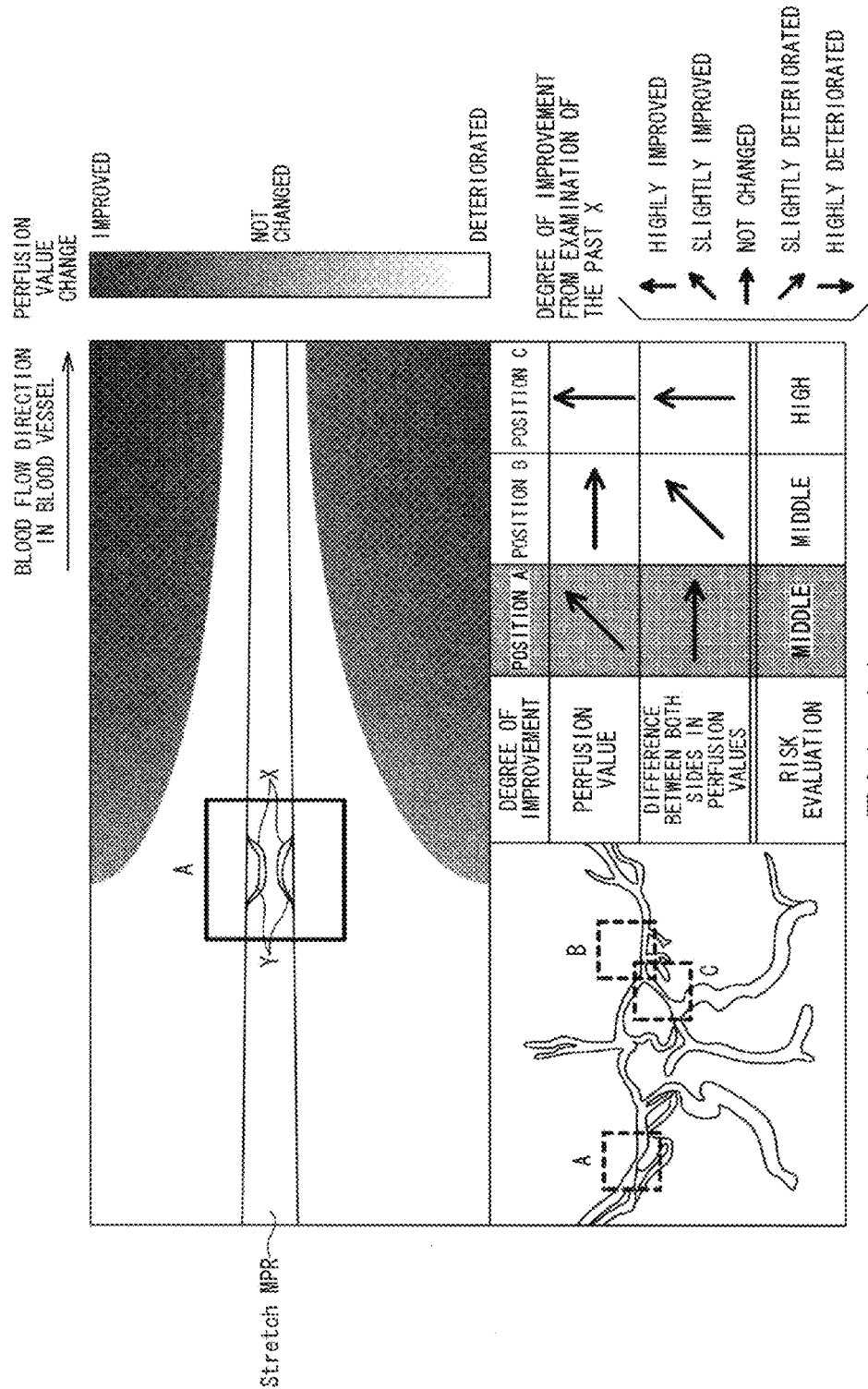
FIG. 11 is a view illustrating exemplary combined display of a composition image of a vascular shape image and a perfusion value image, a list of risk evaluations, and 3D angiogram data.

Also, even in the case where the risk evaluating unit 36 evaluates a risk on the basis of the perfusion value obtained by the perfusion analyzing unit 33 and the difference between the perfusion values of both the sides compared by the comparing unit 35, if an image indicating a difference between the perfusion values obtained in the present examination and the examination of the past is also displayed, conveniently an improved degree of a perfusion value can be easily understood. FIG. 11 illustrates exemplary combined display of a composition image of a vascular shape image and a perfusion value image, a list of risk evaluations, and 3D angiogram data. In FIG. 11, an examination of the past X is compared with a present examination Y. In the composition image of the vascular shape image and the perfusion value image, a vascular shape obtained in the examination of the past X and a vascular shape obtained in the present examination Y at the position A are displayed at a time. For perfusion values, a degree of improvement is displayed on the basis of the difference between the examination of the past X and the present examination Y, calculated by the comparing unit 35. In FIG. 11, as the recovery of the perfusion values is higher, the color becomes darker.

Also, the lists of risk evaluations of the examination of the past X and the present examination Y are compared with each other, and an improved degree from the examination of the past X is displayed. In FIG. 11, improved degrees are represented by arrow directions. For example, at the position A, if lowering of CBV has been slightly improved, an arrow indicated in a diagonally upper direction is displayed, and if a difference of both sides in CBV has not changed, an arrow indicated in a horizontal direction is displayed.

As shown in FIG. 11, if a degree of improvement from an examination of the past is displayed, the user can clearly determine whether a present condition of a contraction portion has been improved or has become worse, which is useful in a future therapeutic plan.

According to the embodiment hereinbefore described, a vascular contraction portion is extracted from a vascular region of 3D angiogram data to generate a two-dimensional vascular shape image, and perfusion analysis is performed on the 3D angiogram data to generate a two-dimensional perfusion value image. The vascular shape image and the perfusion value image are combined with each other and displayed. Thereby, perfusion values in the vascular contraction portion can be judged in a comprehensive manner. Also, a risk of a lesion such as cerebral infraction is evaluated based on a perfusion value of a particular contraction portion and a difference between the perfusion value of the contraction portion and perfusion values of normal positions and thereby quantitative risk evaluation can be performed independent of the subjective.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image processing apparatus comprising:
   an image acquiring unit configured to acquire a three-dimensional medical image;
   a vascular region extracting unit configured to extract a vascular region based on the three-dimensional medical image acquired by the image acquiring unit;
   a vascular shape image generating unit configured to generate an image of a vascular shape of the vascular region extracted by the vascular region extracting unit;
   a perfusion analyzing unit configured to perform perfusion analysis on the three-dimensional medical image acquired by the image acquiring unit so as to obtain a perfusion value indicating a blood circulation condition in tissue around the vascular region;
   a perfusion image generating unit configured to generate an image indicating the perfusion value obtained by the perfusion analyzing unit;
   an image composition unit configured to generate a vascular shape perfusion composition image in which an image generated by the vascular shape image generating unit of the vascular shape in a contraction portion in a blood vessel corresponding to the vascular region is combined with the image indicating the perfusion value generated by the perfusion image generating unit; and
   a display unit configured to display the vascular shape perfusion composition image combined by the image composition unit.

2. The medical image processing apparatus according to claim 1, wherein the image of the vascular shape generated by the vascular shape image generating unit represents a shape of a curved-surface cross-section of the blood vessel along a three-dimensional blood flow direction.

3. The medical image processing apparatus according to claim 2, wherein
   the perfusion image generating unit generates an image indicating the perfusion values of the contraction portion and an area around the contraction portion in the blood vessel based on the perfusion value obtained by the perfusion analyzing unit, and
   the image composition unit combines an image of the shape of the curved-surface cross-section of the blood vessel along the three-dimensional blood flow direction with the image indicating the perfusion values of the contraction portion and the area around the contraction portion in the blood vessel.

4. The medical image processing apparatus according to claim 1, further comprising a contraction region setting unit configured to extract and set the contraction portion of the blood vessel based on the vascular region extracted by the vascular region extracting unit.

5. The medical image processing apparatus according to claim 4, wherein the contraction region setting unit includes
   a vascular center line extracting unit configured to extract a center line of the blood vessel from the medical image acquired by the image acquiring unit,
   a vascular shape extracting unit configured to extract an interior wall of the blood vessel from the medical image acquired by the image acquiring unit,
   an estimated vascular shape calculating unit configured to calculate an estimated interior wall of the blood vessel based on variations in cross-sectional area of the interior wall of the blood vessel along the center line extracted by the vascular center line extracting unit,
   a constriction determining unit configured to determine a constricted region of the blood vessel based on a difference between the interior wall of the present blood vessel extracted by the vascular shape extracting unit and the estimated interior wall of the blood vessel calculated by the estimated vascular shape calculating unit, and
   a vascular contraction determining unit configured to determine whether or not the constricted region of the blood vessel determined by the constriction determining unit is caused by a vascular contraction based on property analysis between an interior wall and an exterior wall of the blood vessel.

6. The medical image processing apparatus according to claim 1, further comprising:
   a region dividing unit configured to divide a medical image of a brain, included in the medical image acquired by the image acquiring unit, into a first region and a second region; and
   a perfusion value difference calculating unit configured to calculate a difference between perfusion values of the first region and the second region.

7. The medical image processing apparatus according to claim 6, further comprising a shape converting unit configured to calculate a displacement of each shape of the first region and the second region divided by the region dividing unit and configured to align the shapes with each other,
   wherein the perfusion value difference calculating unit is configured to, after the shape converting unit aligns the shapes of the first region and the second region with each other, calculate the difference between the perfusion values of the first region and the second region.

8. The medical image processing apparatus according to claim 6, further comprising a risk evaluating unit configured to estimate a risk of the contraction portion in the blood vessel extracted by the contraction region setting unit, based on the perfusion value obtained by the perfusion analyzing unit and the difference between the perfusion values of the first region and the second region calculated by the perfusion value difference calculating unit.

9. The medical image processing apparatus according to claim 8, further comprising a storage unit in which a threshold value of the perfusion value obtained by the perfusion analyzing unit and a threshold value of the difference between the perfusion values calculated by the perfusion value difference calculating unit are stored, wherein the risk evaluating unit is configured to evaluate a risk based on the threshold value of the perfusion value and the threshold value of the difference between the perfusion values stored in the storage unit.

10. The medical image processing apparatus according to claim 8, wherein the display unit is configured to display an image including at least one of the medical image acquired by the image acquiring unit, the vascular shape perfusion composition image combined by the image composition unit, and the risk of the contraction portion evaluated by the risk evaluating unit.

11. The medical image processing apparatus according to claim 10, wherein the display unit displays at least one of the medical image, the vascular shape perfusion composition image, and the risk, corresponding to a predetermined contraction portion.

12. The medical image processing apparatus according to claim 1, further comprising a difference calculating unit configured to calculate a difference between a perfusion value corresponding to a past examination and a perfusion value of a present examination based on a vascular shape perfusion composition image generated from a medical image of an examination executed in the past and the vascular shape perfusion composition image generated from the medical image in the present examination, the perfusion value of the present examination obtained by the perfusion analyzing unit, wherein the display unit is configured to display a combined image of the image indicating the difference between perfusion values corresponding to the past examination and the present examination calculated by the difference calculating unit and the image of the vascular shape.

13. The medical image processing apparatus according to claim 12, further comprising a risk evaluating unit configured to estimate a risk of the contraction portion in the blood vessel based on the perfusion value corresponding to the present examination obtained by the perfusion analyzing unit and the difference between the perfusion values calculated by the difference calculating unit.

14. The medical image processing apparatus according to claim 1, wherein the image composition unit combines the image of the vascular shape in the contraction portion in the blood vessel, a three-dimensional vascular wall image composed of a vascular wall image of the contraction portion in the blood vessel and an image of a vicinity of an exterior wall of the vascular wall of the three-dimensional medical image, and the image indicating the perfusion value with each other so as to generate the vascular shape perfusion composition image.

15. The medical image processing apparatus according to claim 14, wherein the vascular shape perfusion composition image is an image in which the image indicating the perfusion value is combined in a place other than the image of the vascular shape and the three-dimensional vascular wall image.

* * * * *